United States Patent [19]

Kohayakawa

[11] Patent Number: 4,825,873
[45] Date of Patent: May 2, 1989

[54] NON-CONTACT EYE PRESSURE METER

[75] Inventor: Yoshimi Kohayakawa, Yokohama, Japan

[73] Assignee: Canon Kabushiki Kaisha, Tokyo, Japan

[21] Appl. No.: 71,314

[22] Filed: Jul. 9, 1987

[30] Foreign Application Priority Data

Jul. 26, 1986 [JP] Japan .................. 61-176169

[51] Int. Cl.$^4$ ............................................. A61B 3/16
[52] U.S. Cl. .................................................. 128/648
[58] Field of Search .................. 128/648, 652, 645

[56] References Cited

U.S. PATENT DOCUMENTS

| | | | |
|---|---|---|---|
| 3,232,099 | 2/1966 | Motchenbacher | 128/648 |
| 3,304,769 | 2/1967 | Stauffer | 128/648 |
| 3,538,754 | 11/1970 | Grolman et al. | 128/648 |
| 3,756,073 | 9/1973 | Lavallee et al. | 128/648 |
| 3,832,890 | 9/1974 | Grolman et al. | 128/648 |

FOREIGN PATENT DOCUMENTS 61-16729 1/1986 Japan.

*Primary Examiner*—Edward M. Coven
*Attorney, Agent, or Firm*—Fitzpatrick, Cella, Harper & Scinto

[57] ABSTRACT

A non-contact eye pressure meter is provided with a cornea deforming system for blowing a compressed fluid of a pressure variable with time against the cornea of an eye to be examined from a nozzle provided in a predetermined optical member opposed to the eye to be examined, and a deformation detecting system for applying a light beam from a predetermined light source to the eye to be examined past only one area of the interior of the nozzle and the interior of the predetermined optical member which is in the outer peripheral portion of the nozzle and receiving the cornea-reflected light by a predetermined light-receiving element past only the other area. The light source and the light-receiving element are set optically substantially conjugately through corneal reflection when the cornea of the eye to be examined is deformed to a predetermined curvature.

11 Claims, 5 Drawing Sheets

NON-CONTACT EYE PRESSURE METER

BACKGROUND OF THE INVENTION

1. Field of the Invention

This invention relates to a non-contact eye pressure meter for blowing, for example, air against the cornea of an eye to be examined to thereby deform the cornea and detecting the deformation thereof, for example, photoelectrically.

2. Related Background Art

The prior-art eye pressure meter of this type is known from U.S. Pat. No. 3,585,849 and U.S. Pat. No. 3,756,073 wherein as shown in FIG. 1A of the accompanying drawings, the air from an air cylinder mechanism 1 is blown as an air stream against the cornea Ec of an eye E to be examined through a nozzle 2a in an objective lens 2. It is usually the case that such meter is provided with a cornea deformation detecting system for projecting a light onto the cornea Ec from an oblique direction and receiving the cornea-reflected light in an oblique direction. That is, the light from a light source 3 such as a light-emitting diode is projected onto the cornea Ec of the eye E to be examined form an oblique direction through a projection optical system 4, and the reflected light therefrom is received by a photoelectric light-receiving element 6 from an oblique direction through a light-receiving optical system 5. Reference numeral 7 designates a finder optical system.

The prior-art eye pressure meter has a disadvantage that its structure is unavoidably complicated bacause both the projection optical system 4 and the light-receiving optical system 5 are disposed in oblique directions relative to the cornea Ec.

Also, U.S. Pat. No. 3,832,890 discloses, as shown in FIG. 1B of the accompanying drawings, the provision of a cornea deformation detecting system for projecting a light onto the cornea Ec from the direction of the optic axis and receiving the cornea-reflected light in the direction of the optic axis. That is, the light emitted from a light source 3a irradiates the cornea Ec so as to travel toward the focus of the cornea Ec through a lens 7a and an objective lens 2, and the light reflected by the cornea Ec is received by a photoelectric light-receiving element 6a through the lens 7a and the objective lens 2.

However, in U.S. Pat. No. 3,832,890, the light source 3a and the photoelectric light-receiving element 6a are in conjugate relationship with respect to the optical system whose reflecting surface is provided by the cornea before deformed and therefore, the deformation of the cornea cannot be recognized with good accuracy.

Moreover, the applied light beam passing through the interior of the nozzle 2a and the applied light beam passing through the exterior of the nozzle 2a differ in situation from each other and therefore, it is possible that random light is picked up when the deformation of the cornea is detected.

SUMMARY OF THE INVENTION

It is an object of the present invention to solve the above-noted problems and to provide a non-contact eye pressure meter which is capable of accurately detecting any deformation of cornea and improving measurement accuracy while maintaining compactness.

It is also an object of the present invention to provide a non-contact eye pressure meter which finds the eye pressure at a point of time whereat the deformation of cornea is little, thereby alleviating the shock to an eye to be examined.

DESCRIPTION OF THE PREFERRED EMBODIMENT

The present invention will hereinafter be described in detail with respect to various embodiments thereof shown in FIGS. 2 to 9.

Figure 1A:
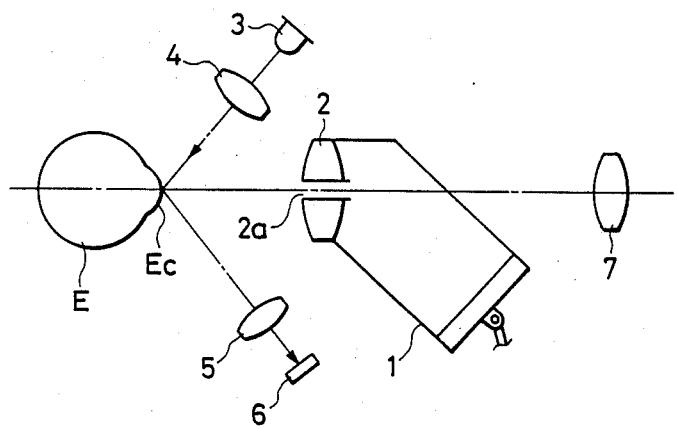
FIGS. 1A and 1B show the prior art.
Figure 1B:
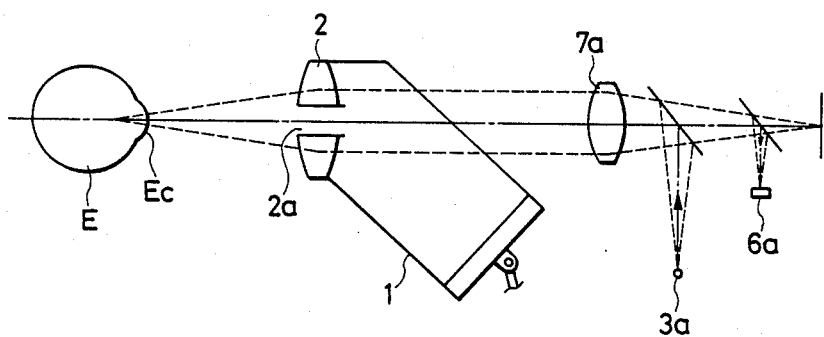
Figure 2:
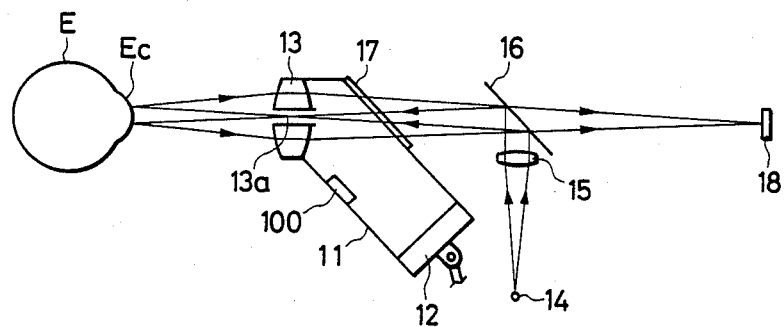
FIGS. 2, 3, 6 and 7 show an embodiment in which the light beam is passed inside of a nozzle and the light reflected by the cornea is received from the outside of the nozzle.

In FIG. 2, as in the prior art, the air in an air compressing chamber 11 is forced out by a piston 12 so as to be pressure variable with time and is blown against the cornea Ec of an eye E to be examined from a nozzle 13a attached to an objective lens 13. The light beam from a light source 14 is condensed by a lens 15, is further reflected through a beam splitter member 16 toward the eye E to be examined, and is projected onto the cornea Ec through a window 17 and the nozzle 13a of the objective lens 13. Also, the reflected light beam from the cornea Ec passes through the lens portion of the objective lens 13 which is around the nozzle 13a, and is received by a photoelectric light-receiving element 18 which is disposed at a position where the reflected light from the cornea Ec is condensed when the cornea Ec is of a predetermined curvature, for example, the radius of curvature r thereof is 15 mm.

In the construction of FIG. 2, when the piston 12 is moved in the air compressing chamber 11, the air passes through the nozzle 13a of the objective lens 13 and is blown as an air stream against the cornea Ec. When the air pressure becomes higher with time and the air pressure on the cornea Ec exceeds the pressure in the eye, the cornea Ec begins to be deformed and the deformation begins so that the radius of curvature thereof becomes greater. The light beam emitted from the light source 14 and reflected by the cornea Ec is adapted to be condensed on the light-receiving surface of the photoelectric light-receiving element 18 when the cornea Ec assumes a predetermined curvature, and therefore, the time when the air stream is blown and the signal of the photoelectric light-receiving element 18 becomes maximum is the time when the air pressure and the eye pressure are balanced with each other, and it is possible to measure the eye pressure of the eye E to be examined by the air pressure at this point of time. Instead of the time measurement, a pressure sensor 100 may be provided in the air compressing chamber 11 and the eye pressure may be measured from the output of the pressure sensor 100 when the signal of the photoelectric light-receiving element 18 becomes a maximum.

The radius of curvature of a normal cornea Ec is 7–8 mm and therefore, if the aforementioned predetermined curvature is set to a curvature of the order of 10–20 mm, the incipient stage of the deformation will be attained as compared with the conventional pressure level and therefore, the measurement will not be liable to be affected by eyeball hardness such as the elasticity of the cornea itself.

Figure 3:
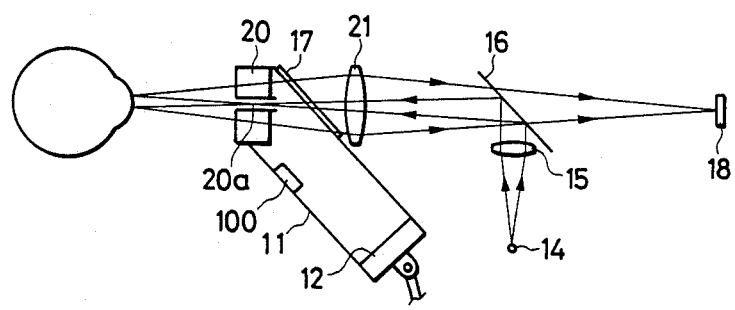

FIG. 3 shows a second embodiment of the present invention. In FIG. 3, like reference numerals designate like members. In this embodiment, planar glass 20 having a nozzle 20a therein is provided at the position of the objective lens 13, and a lens 21 disposed between the air compressing chamber 11 and the beam splitter member 16 functions as an objective lens.

Figure 4:
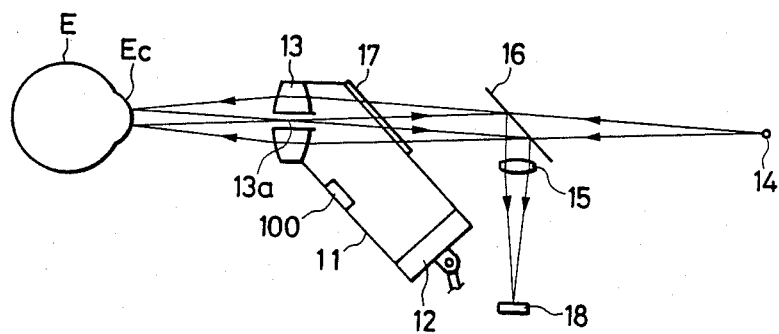
FIGS. 4, 5, 8 and 9 show embodiments in which the light beam is passed the outside of a nozzle and the light reflected by the cornea is received from the inside of the nozzle.

FIG. 4 shows a third embodiment in which the positions of the light source 14 and the photoelectric light-receiving element 18 in the embodiment shown in FIG. 2 are interchanged with each other.

Figure 5:
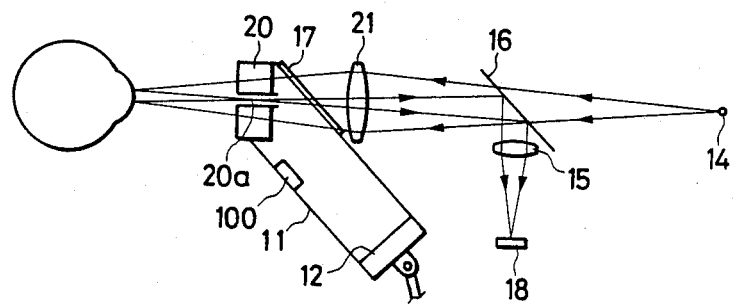

FIG. 5 shows a fourth embodiment in which the positions of the light source 14 and the photoelectric light-receiving element 18 in the embodiment shown in FIG. 3 are interchanged with each other.

Figure 6:
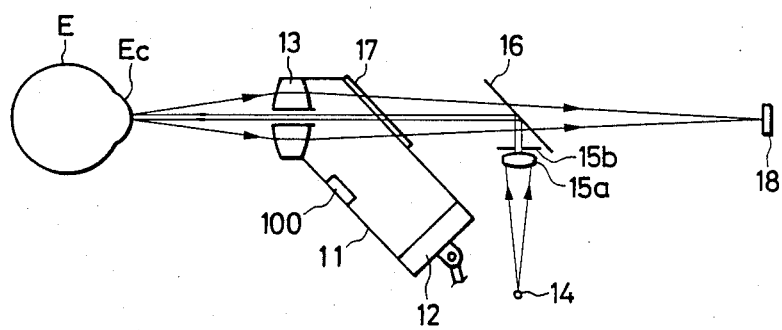

While in the above-described embodiments, a divergent light beam or a convergent light beam is used as the light beam applied to the eye to be examined, a fifth embodiment as shown in FIG. 6 is also possible in which a parallel light beam is used as the light beam applied to the eye to be examined and the parallel beam passes through the interior of the nozzle. In FIG. 6, the light source 14 lies at the focus position of a lens 15a and a parallel light beam emerging from the lens 15a passes through a stop 15b and through the nozzle in the bore portion of the objective lens 13.

Figure 7:
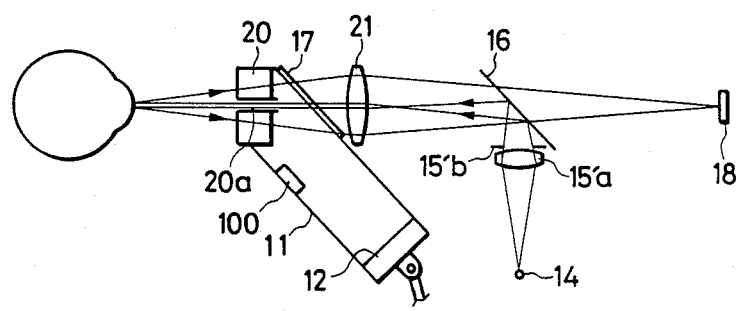

FIG. 7 shows a sixth embodiment in which a light emitted from the light source 14 passes through a lens 15'a and a stop 15'b, is imaged at the focus position of a lens 21, emerges as a parallel light beam from the lens 21 and passes through a nozzle 20a provided in planar glass 20.

Figure 8:
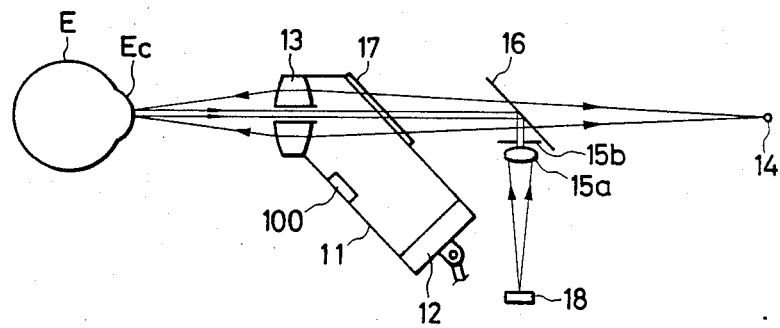

FIG. 8 shows a seventh embodiment in which the positions of the light source 14 and the photoelectric light-receiving element 18 in the embodiment shown in FIG. 6 are interchanged with each other.

Figure 9:
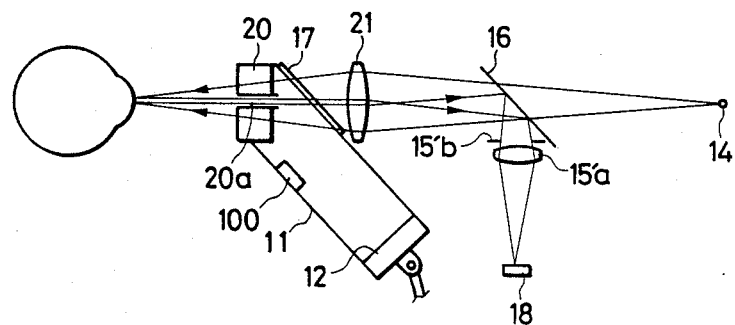

FIG. 9 shows an eighth embodiment in which the positions of the light source 14 and the photoelectric light-receiving element 18 in the embodiment shown in FIG. 7 are interchanged with each other.

As described above, according to the present invention, there is provided a non-contact eye pressure meter which can accurately detect any deformation of cornea to thereby improve measurement accuracy while maintaining compactness and moreover find the eye pressure at a point of time whereat the deformation of cornea is little, thereby alleviating the shock to the eye to be examined.

I claim:

1. A non-contact eye pressure meter comprising:
a cornea deforming system for blowing a compressed fluid of a pressure variable with time against the cornea of an eye to be examined from a nozzle opposed to the cornea of the eye to be examined; and
a deformation detecting system for projecting a light beam from a light source to the eye to be examined on a path located either on the side inside of said nozzle and the side outside of said nozzle and receiving said light beam reflected by the cornea of the eye to be examined by a light-receiving element past the side of said nozzle opposite that for the applying light beam;
said light source and said light receiving element being set substantially optically conjugate by way of both the cornea of the eye to be examined and an imaging optical system in the optical path when the cornea of the eye to be examined is deformed to a predetermined convex curvature before applanation.

2. A non-contact eye pressure meter according to claim 1, wherein said nozzle is provided in an objective lens opposed to the eye to be examined and said objective lens is contained in said imaging optical system.

3. A non-contact eye pressure meter according to claim 1, wherein said nozzle is provided in a transparent planar plate opposed to the eye to be examined.

4. A non-contact eye pressure meter according to claim 1, further including condensing means for condensing the light beam from said light source substantially at a location inside of said nozzle and for applying a divergent light beam from said location to the cornea of the eye to be examined.

5. A non-contact eye pressure meter according to claim 1, further including condensing means for condensing the cornea-reflected light beam substantially at a location inside of said nozzle when the cornea of the eye to be examined is deformed to said predetermined curvature.

6. A non-contact eye pressure meter according to claim 1, wherein said deformation detecting system includes parallel projection means for projecting parallel light beams through the interior of said nozzle and for irradiating the cornea of the eye to be examined.

7. A non-contact eye pressure meter according to claim 1, wherein said deformation detecting means includes means for forming the light beams reflected by the cornea of the eye to be examined parallel to an axis of said nozzle when the cornea of the eye to be examined is deformed to the predetermined curvature.

8. A non-contact eye pressure meter according to claim 1, wherein said light-receiving means is adapted to provide a maximum output signal, and the pressure meter further includes calculating means for calculating the eye pressure when said light receiving means provides the maximum output signal.

9. A non-contact eye pressure meter according to claim 1, wherein said light-receiving means is adapted to provide a maximum output signal, and
said deforming system is provided with a cylinder having a pressure sensor for sensing the eye pressure when said light-receiving element provides the maximum output signal.

10. A non-contact eye pressure meter comprising:
a cornea deforming system for blowing a compressed fluid of a pressure variable with time against the cornea of an eye to be examined from nozzle opposed to the cornea of the eye to be examined; and
a deformation detecting system for projecting a light beam from a light source to the eye to be examined on a path located in one of either the side inside of said nozzle and the side outside of said nozzle and receiving said light beam reflected by the cornea of the eye to be examined by a light-receiving element, said reflected light beam travelling on a path located on the side of said nozzle opposite that for the applying light beam, said light source and said light-receiving element being set substantially optically conjugate by way of both the cornea of the eye to be examined and an imaging optical system in the optical path when the cornea of the eye to be examined is deformed a predetermined shape.

11. A non-contact eye pressure meter comprising:
a cornea deforming system for blowing a compressed fluid of a pressure variable with time against the cornea of an eye to be examined from a nozzle opposed to the cornea of the eye to be examined; and a deformation detecting system for projecting a light beam from a light source to the eye to be examined and receiving said light beam reflected by the cornea of the eye to be examined by a light-receiving element, said light source and said light-receiving element being set substantially optically conjugate by way of both the cornea of the eye to be examined and an imaging optical system in the optical path when the cornea of the eye to be examined is deformed to a predetermined convex curvature before applanation.

* * * * *

UNITED STATES PATENT AND TRADEMARK OFFICE
CERTIFICATE OF CORRECTION

PATENT NO. : 4,825,873
DATED : May 2, 1989
INVENTOR(S) : YOSHIMI KOHAYAKAWA

It is certified that error appears in the above-identified patent and that said Letters Patent is hereby corrected as shown below:

COLUMN 1

Line 24, "form" should read --from--.
Line 32, "bacause" should read --because--.
Line 51, "deformed" should read --being deformed--.

COLUMN 2

Line 11, "the outside" should read --outside--.

COLUMN 4

Line 49, "from nozzle" should read --from a nozzle--.
Line 64, "deformed a" should read --deformed to a--.

Signed and Sealed this

Twenty-eighth Day of May, 1991

Attest:

HARRY F. MANBECK, JR.

Attesting Officer

Commissioner of Patents and Trademarks